United States Patent [19]

Schroeder et al.

[11] 4,163,747

[45] Aug. 7, 1979

[54] PROCESS FOR THE PREPARATION OF 1-ALKYLAMINO-ANTHRAQUINONES

[75] Inventors: Bernd Schroeder, Odenthal; Rudolf Braden, Odenthal-Scheuren; Wolfgang Auge; Karl-Werner Thiem, both of Cologne; Rütger Neeff, Leverkusen, all of Fed. Rep. of Germany

[73] Assignee: Bayer Aktiengesellschaft, Leverkusen, Fed. Rep. of Germany

[21] Appl. No.: 944,935

[22] Filed: Sep. 22, 1978

Related U.S. Application Data

[63] Continuation of Ser. No. 806,406, Jun. 14, 1977, abandoned.

[30] Foreign Application Priority Data

Jul. 1, 1976 [DE] Fed. Rep. of Germany ....... 2629524

[51] Int. Cl.$^2$ .............................................. C07C 97/24
[52] U.S. Cl. ...................................... 260/378; 260/689
[58] Field of Search ................................ 260/378, 689

[56] References Cited

U.S. PATENT DOCUMENTS

| | | | |
|---|---|---|---|
| 3,491,126 | 1/1970 | Schwander et al. ................. | 260/378 |
| 3,931,253 | 1/1976 | Krehmueller et al. .............. | 260/378 |
| 4,000,167 | 12/1976 | Hohmann et al. .................. | 260/378 |
| 4,021,456 | 5/1977 | Seha .................................... | 260/378 |

FOREIGN PATENT DOCUMENTS

| | | | |
|---|---|---|---|
| 50-63017 | 5/1975 | Japan ....................................... | 260/378 |
| 461427 | 2/1937 | United Kingdom ..................... | 260/378 |

OTHER PUBLICATIONS

*Anthracene and Anthraquinone,* E. de Barry, Barnett, D. Van Nostrand Comp., N.Y. 1921, pp. 198–199.

*Primary Examiner*—Allen B. Curtis
*Assistant Examiner*—Raymond Covington
*Attorney, Agent, or Firm*—Sprung, Felfe, Horn, Lynch & Kramer

[57] ABSTRACT

Process for the preparation of 1-alkylamino-anthraquinones which comprises reacting 1-nitroanthraquinone with a monoalkylamine in the presence of an ether, a hydrocarbon or a mixture of an ether and a hydrocarbon. The 1-alkylamino-anthraquinones which are obtained can be employed directly as dyestuffs or used, without further purification, for the production of dyestuffs. Process of the invention results in the procurement of 1-alkylamine-anthraquinones of high purity and in high yield and avoids the formation of undesired by-products.

10 Claims, No Drawings

PROCESS FOR THE PREPARATION OF 1-ALKYLAMINO-ANTHRAQUINONES

This is a continuation of application Ser. No. 806,406, filed June 14, 1977, now abandoned.

The present invention relates to a process for the preparation of 1-alkylamino-anthraquinones by reacting 1-nitroanthraquinone with monoalkylamines.

It is already known that monoalkylated aminoanthraquinones can be prepared from nitroanthraquinones by reaction with monoalkylamines (German Patent Specification 144,634). In this process the reaction of the nitro-anthraquinones with monoalkylamines is carried out in the presence of excess amine, pyridine or alcohol as the solvent. The reactions are carried out at elevated temperature and optionally under pressure. Working up is carried out by filtering off the reaction product which has crystallised out.

A disadvantage of this process is that, in general, the alkylaminoanthraquinones obtained are not sufficiently pure for further processing to dyestuffs since the undesired by-products which arise during the reaction are not completely removed with the mother liquor. Furthermore, the solubility of some alkylamino-anthraquinones in alcohol, but especially in pyridine or excess amine, is considerable, so that only low yields are achieved. Moreover, complete conversion requires long reaction times, for example 5 hours are required for the reaction of 1-nitro-2-methylanthraquinone with methylamine in pyridine in a closed vessel at 100° C.

In addition, alcohol and pyridine are disadvantageous as solvents since, as a result of their hydrophilic character, they can lead, after working up, to considerable loads on the effluents.

A process for the preparation of 1-alkylamino-, 1-dialkylamino- and 1-arylamino-anthraquinones by reacting 1-nitroanthraquinone with alkylamines, dialkylamines or arylamines is described in Japanese Published Specification 75/63,017. The reaction is carried out in an aromatic solvent at temperatures of 50°–150° C. optionally with the addition of neutralising agents such as sodium hydroxide, potassium hydroxide, sodium carbonate, sodium bicarbonate or sodium acetate. In this case the reaction times are 5–10 hours.

However, when carried out on an industrial scale this process is uneconomical since the long reaction times lead to only low space-time yields. Moreover, at the reaction temperatures used, the N-alkylammonium nitrites which are produced during the reaction and are formed from the nitrous acid liberated and excess alkylamine are able to accumulate largely undecomposed. If, for example, the reaction of 1-nitro-anthraquinone with excess methylamine is carried out at 90° C., considerable amounts of N-methylammonium nitrite can be formed after 3–5 hours. On subsequent warming this can lead to substantial evolution of gas and heat and thus to explosions.

A process for the preparation of pure 1-alkylamino-anthraquinones has now been found which is characterised in that the reaction of 1-nitro-anthraquinone with monoalkylamines is carried out in the presence of an ether or of a hydrocarbon or of a mixture of these compounds.

The 1-alkylamino-anthraquinones prepared in this way can be further processed without further purification, for example without recrystallisation, to give dyestuffs.

Suitable solvents are, for example, aliphatic ethers particularly dialkyl ethers or dialkyl ethers of ethylene glycol with 4 to 12 C atoms, such as diethyl ether, di-sec.-butyl ether, di-isopentyl ether, ethylene glycol dimethyl ether, diethylene glycol dimethyl ether, diethylene glycol diethyl ether, diethylene glycol di-n-butyl ether, butyl-methyl ether and glycol methylene ether; and also cycloaliphatic ethers with 4 to 12 C atoms, such as methoxycyclohexane, ethoxycyclohexane, dicyclohexyl ether, tetrahydrofurane and dioxane, as well as carbocyclic aromatic ethers with 7 to 14 C atoms, such as anisole, phenetole, diphenyl ether, 2-methoxynaphthalene, amyl phenyl ether and aralkyl ethers with 8 to 14 C atoms, such as benzyl isoamyl ether, dibenzyl ether and methyl benzyl ether.

Aliphatic ethers, such as ethylene glycol dimethyl ether, diethylene glycol dimethyl ether and diethylene glycol diethyl ether, and cycloaliphatic ethers, such as methoxycyclohexane, dicyclohexyl ether, tetrahydrofurane and dioxane, as well as aromatic ethers, such as anisole and phenetole, are particularly suitable.

Examples of suitable hydrocarbons which are liquid at the reaction temperature are aliphatic and cycloaliphatic hydrocarbons with 5 to 20 C atoms, such as n-pentane, n-hexane, n-heptane, cyclohexane, methylcyclohexane, cyclododecane, decalin, cycloheptane, cyclopentane, n-decane 1,2-dimethylcyclohexane, 1,3-dimethylcyclohexane, 1,4-dimethylcyclohexane, 2,2-dimethylpentane, 2,3-dimethylpentane, 2,4-dimethylpentane, 3,3-dimethylpentane, isopropylhexane, methylcyclohexane, 2-methylheptane, 3-methylheptane, 4-methylheptane, 2-methylhexane, 3-methylhexane, 2-methyl-octane, 3-methyl-octane, 4-methyl-octane, 2-methyl-pentane, 3-methyl-pentane, n-octane, penta-isobutane, triethylmethane, 2,2,3-trimethylpentane, 2,2,4-trimethyl-pentane and 2,4,4-trimethyl-pentane.

Aliphatic and cycloaliphatic hydrocarbons with 6 to 12 C atoms, such as n-hexane, n-heptane, decalin, cyclohexane and dodecane, are preferably employed in the process according to the invention.

Further suitable hydrocarbons are aromatic hydrocarbons, for example mononuclear and binuclear aromatic hydrocarbons. These can be monosubstituted or polysubstituted by alkyl radicals, each with up to 12 C atoms, such as methyl, ethyl, n-propyl iso-propyl, isoamyl or isododecyl. Examples of aromatic hydrocarbons which may be mentioned are: benzene, toluene, o-, m- and p-xylene, isopropylbenzene, trimethylbenzene, diethylbenzene, tetramethylbenzene, di-iso-propylbenzene, isododecylbenzene, tetralin, naphthalene, methylnaphthalene, diphenyl, diphenylmethane, o-, m- and p-cymene, dibenzyl,dihydronaphthalene, 2,2'-dimethyldiphenyl, 2,3'-dimethyl-diphenyl, 2,4'-dimethyl-diphenyl, 3,3'-dimethyl-diphenyl, 1,2-dimethylnaphthalene, 1,4-dimethylnaphthalene, 1,6-dimethylnaphthalene, 1,7-dimethylnaphthalene, 1,1-diphenyl-ethane, hexamethylbenzene, isoamylbenzene, pentamethylbenzene, 1,2,3,4-tetramethylbenzene, 1,2,3,5-tetramethylbenzene, 1,2,7-trimethylnaphthalene and 1,2,5-trimethylnaphthalene.

Preferred aromatic hydrocarbons are: benzene, toluene, o-, m- and p-xylene, 1,3,5-trimethylbenzene and isopropylbenzene.

In addition to the solvents mentioned above, mixtures of these solvents can also be employed in the process according to the invention.

Monoalkylamines suitable for the reaction with 1-nitro-anthraquinone are amines with, for example, up to 12 C atoms, especially methylamine, ethylamine, n- or iso-propylamine, n-, iso- or tert.-butylamine, cyclopentylamine, hexylamine, cyclohexylamine and dodecylamine. Particularly preferred monoalkylamines for the process according to the invention are, for example, methylamine, ethylamine, iso-propylamine, iso-butylamine and cyclohexylamine.

The 1-alkylamino-anthraquinones prepared by the process according to the invention can contain alkyl groups with up to 12 C atoms, for example methyl, ethyl, n- or iso-propyl, n-, iso- or tert.-butyl, hexyl or cyclohexyl or dodecyl groups. Compounds preferably prepared by the process according to the invention are methyl-, ethyl-, iso-propyl-, iso-butyl- and cyclohexyl-aminoanthraquinone.

The process according to the invention is generally carried out at temperatures of from about 150 to about 220° C. and preferably of 160° to 200° C. The molar ratio of alkylamine to 1-nitro-anthraquinone which is initially introduced is, in general, at least 2:1. Preferably, this molar ratio is in the range of 2.5:1 to 40:1 and especially in the range of 3:1 to 25:1. Here and in the text which follows, molar ratio is understood as the molar ratio of alkylamine to 1-nitro-anthraquinone.

The process according to the invention can be carried out under normal pressure or elevated pressure, for example under pressures of up to 100 bars. Pressures in the range of 2 to 50 bars are preferred.

The process according to the invention can be carried out by initially introducing the monoalkylamine in excess and metering in the 1-nitroanthraquinone together with the solvent, or by initially introducing 1-nitroanthraquinone with the solvent and adding the monoalkylamine.

The reaction time depends on the temperature, the pressure, the molar ratio and the nature of the alkylamine employed. In general, the rate of reaction increases with increasing temperature and increasing molar ratio of alkylamine to 1-nitroanthraquinone. The reaction times are in general less than 2 hours.

The process can be carried out continuously or discontinously.

The reaction mixture can be worked up according to customary methods, for example by filtering off the product which, after cooling to room temperature, has crystallised out from the organic solvent. The mother liquor thus obtained can be recycled into the process.

However, the reaction mixture can also be worked up by distilling off the solvent or, alternatively, with the aid of a diluent which lowers the solubility of the 1-alkylamino-anthraquinone in the reaction solution, for example petroleum ether, chloroform or water so that 1-alkylamino-anthraquinone is precipitated.

In general, further purification, for example by recrystallisation, of the products obtained by the process according to the invention is not necessary.

Compared with the known processes for the preparation of 1-alkylamino-anthraquinones by reacting 1-nitro-anthraquinone with monoalkylamines, the process according to the invention has the advantage that the process can be carried out particularly economically, that is to say with short reaction times and with high space-time yields and also without an additional load on the effluent. The 1-alkylamino-anthraquinones obtained in this way are isolated in high purity. Moreover, with the process according to the invention the formation of undesired by-products, which can have an adverse influence on the course of the reaction, is avoided.

The 1-alkylamino-anthraquinones can be employed directly as dyestuffs (C.I. 60505) or serve as valuable intermediate products for the preparation of dyestuffs (C.I. 68215, 68200, 68205, 68220 and 68500).

EXAMPLE 1

105 g of 1-nitro-anthraquinone (99% pure ) and 1.12 l of o-xylene are heated to 170° C. in an autoclave of 3 l capacity. 193 g of methylamine (molar ratio 15:1) are metered in in the courser of 20 minutes and during this time the temperature is not allowed to rise above 170° C. The reaction is brought to completion at this temperature and under a pressure of 33 bars in the course of 20 minutes. The reaction mixture is let-down and methylamine and o-xylene are distilled off. The residue is dried.

Yield: 79.3 g (96% of theory) of a 96.3% pure 1-methyl-aminoanthraquinone.

Similar yields and purities are obtained when toluene, benzene, 1,3,5-trimethylbenzene, isopropylbenzene, isododecylbenzene, diphenylmethane, n-hexane, n-heptane, decalin, tetralin, methylcyclohexane, cyclododecane, di-n-propyl ether, dibutyl ether, diethylene glycol dimethyl ether, diethylene glycol diethyl ether, methoxycyclohexane, dicyclohexyl ether, anisole, phenetole, diphenyl ether, tetrahydrofurane or dioxane, or mixtures of these solvents, are used in place of o-xylene.

EXAMPLE 2

419 g of 1-nitro-anthraquinone (99% pure) are reacted with 205 g of methylamine (molar ratio 4:1) in 1.48 l of o-xylene under a pressure of 66 bars and at a temperature of 170° C. in the course of 35 to 40 minutes.

The reaction mixture is worked up as in Example 1. 347.9 g (97% of theory) of a 95% pure 1-methylamino-anthraquinone are obtained.

EXAMPLE 3

765 g of 1-nitro-anthraquinone (99% pure), together with 3.4 l of o-xylene, are initially introduced into an autoclave of 5 l capacity and heated to 160° C. 375 g of methylamine (molar ratio 4:1) are metered in at this temperature in the course of 25 minutes. The reaction is brought to completion in the course of 30 minutes under a pressure of 85 bars and at a temperature of 170° C. After working up as in Example 1, 685 g (96.5% of theory) of a 98.3% pure 1-methylamino-anthraquinone are obtained.

EXAMPLE 4

90 g of ethylamine (molar ratio 10:1) are metered into 50.6 g of 1-nitro-anthraquinone (99% pure) in 240 ml of o-xylene in a 0.7 l autoclave. The reaction has ended after 80 minutes at a temperature of 140° C. and under a pressure of 35 bars.

The reaction mixture is allowed to cool and the residue is filtered off, washed with a little xylene and dried. 45.7 g (91% of theory) of 1-ethylamino-anthraquinone are obtained. No starting material can be detected by chromatography.

EXAMPLE 5

A mixture of 50.6 g of 1-nitro-anthraquinone (99% pure) and 240 ml of o-xylene is reacted with 118 g of n-propylamine (molar ratio 10:1) at a temperature of 170° C. and under a pressure of 30 bars and for a reaction time of 80 minutes. Working up analogously to Example 1 gives 50 g (94% of theory) of 1-n- propylamino-anthraquinone, in which no further 1-nitro-anthraquinone can be detected.

EXAMPLE 6

Without the application of pressure, 2.5 hours at 144° C. are required in order to effect complete reaction of 25.3 g of 1-nitro-anthraquinone with 23.6 g of n-propylamine (molar ratio 4:1) in 150 ml of o-xylene. The reaction mixture is worked up analogously to Example 1.

EXAMPLE 7

60.3 g of 1-nitro-anthraquinone and 300 ml of o-xylene are pre-heated to 170° C. in an autoclave of 0.7 l capacity. 141 g of isopropylamine (molar ratio 10:1) are then metered in in the course of 5 minutes. The reaction mixture is kept at a temperature of 170° C. and under a pressure of 48 bars for a further 45 minutes.

The reaction mixture is worked up analogously to Example 1. 60 g (96% of theory) of 1-isopropylamino-anthraquinone of 97% purity are obtained.

EXAMPLE 8

76 g of 1-nitro-anthraquinone (99% pure) and 350 ml of o-xylene are warmed to 160° C. in a 0.7 l autoclave. 44.4 g of isopropylamine (molar ratio 2.5:1) are metered in at this temperature. The mixture is warmed to 170° C. The reaction has ended after 45 minutes under 30 bars.

The reaction mixture is worked up as in Example 1.

Yield: 76.5 g (97% of theory) of 1-isopropylamino-anthraquinone.

Purity: 97.6%

EXAMPLE 9

384 g of isopropylamine and 1,390 g of o-xylene are initially introduced into a stainless steel autoclave, which has a capacity of 5 l and is fitted with a stirrer and steam jacket heating, and are heated to 165° C. A suspension of 543 g of 1-nitroanthraquinone with a purity of 98.4% by weight in 815 g of o-xylene is injected into the autoclave in the course of 20 minutes (molar ratio 3:1). During the addition the pressure rises from 10 to 40 bars and the temperature rises from 165 to 170° C. The reaction has ended after a further 30 minutes at 170° C. After cooling and letting-down, the residual solution is evaporated. 548 g of 1-isopropylaminoanthraquinone with a purity of more than 98% are obtained.

EXAMPLE 10

63.3 g of 1-nitroanthraquinone (99% pure) in 320 ml of cyclohexane are reacted with 147.8 g of isopropylamine (molar ratio 10:1) for 70 minutes at a temperature of 160° C. and under a pressure of 50 bars. Working up analogously to Example 1 gives 62 g (94.5% of theory) of 97.6% pure 1-isopropylamino-anthraquinone.

EXAMPLE 11

If 63.3 g of 1-nitro-anthraquinone (99% pure) are reacted with 73.9 g of isopropylamine (molar ratio 5:1) in 300 ml of ethylene glycol dimethyl ether at a temperature of 175° C. and under a pressure of 45 bars for 40 minutes and, after cooling and letting-down, the reaction mixture is poured into water and the residue is filtered off, this gives, after drying, 39.7 g (91% of theory) of a 97% pure 1-isopropylamino-anthraquinone.

EXAMPLE 12

25.3 g of 1-nitroanthraquinone (99% pure) in 120 ml of p-cymene are boiled together with 29.8 g of cyclohexylamine (molar ratio 3:1) for 2 hours under reflux. After cooling the reaction mixture, 150 ml of petroleum ether are added, the mixture is filtered and the residue is washed with petroleum ether and dried. 28.1 g (94% of theory) of cyclohexylamino-anthraquinone are obtained. No further starting material can be detected by means of thin layer chromatography.

What is claimed is:

1. Process for the preparation of a 1-alkylamino-anthraquinone, which comprises reacting 1-nitroanthraquinone with a monoalkylamine in molar ratios of alkylamine to 1-nitroanthraquinone of at least 2:1 at 150°–220° C. in the presence of an ether or of a hydrocarbon or of a mixture of these compounds and separating the 1-alkylamino-anthraquinone from the reaction mixture.

2. Process according to claim 1, characterised in that aliphatic or cycloaliphatic or aromatic ethers with up to 14 C. atoms are used.

3. Process according to claim 1, characterised in that tetrahydrofurane, dioxane, ethylene glycol dimethyl ether, diethylene glycol dimethyl ether, diethylene glycol diethyl ether, methoxycyclohexane, dicyclohexyl ether, anisole or phenetole is used as the ether.

4. Process accordingr to claim 1, characterised in that aliphatic cycloaliphatic or aromatic hydrocarbons or mixtures of them, which can optionally be substituted by alkyl, with up to 20 C atoms are used as the huydrocarbon.

5. Process according to claim 1, characterised in that n-hexane, n-heptane, dodecane, cyclohexane, decaline, benzene, toluene, o-, m- or p-xylene, 1,3,5-trimethylbenzene or isopropyl-benzene is used as the hydrocarbon.

6. Process according to claim 1, characterized in that monoalkylamines with up to 12 C atoms are employed in the reaction.

7. Process according to claim 1, characterized in that methylamine, ethylamine, iso-propylamine, iso-butylamine or cyclohexylamine is employed in the reaction.

8. Process according to claim 1, characterised in that, in an aromatic hydrocarbon with 6 to 10 carbon atoms, the reaction with a monoalkylamine with up to 6 C atoms is carried out at 160° C. to 200° C. and under pressures of up to 100 bars.

9. Process according to claim 1, characterised in that the reaction is carried out using molar ratios of alkylamine to 1-nitro-anthraquinone within the range of from 2,5:1 to 40:1.

10. Process according to claim 1, characterised in that the reaction is carried out using molar ratios of alkylamine to 1-nitro-anthraquinone within the range of from 3:1 to 25:1.

* * * * *

UNITED STATES PATENT AND TRADEMARK OFFICE
CERTIFICATE OF CORRECTION

PATENT NO. : 4,163,747
DATED : August 7, 1979
INVENTOR(S) : Bernd Schroeder, et al.

It is certified that error appears in the above-identified patent and that said Letters Patent are hereby corrected as shown below:

Column 4, line 10 delete "in" 2nd occurr. and "courser" should be --course--.

Column 6, line 33, accordingr" should be --according--.

Column 6, line 36, "huydro-" should be --hydro- --.

Column 6, line 34, after "aliphatic" insert --,--.

Signed and Sealed this

Fourth Day of March 1980

[SEAL]

Attest:

SIDNEY A. DIAMOND

Attesting Officer

Commissioner of Patents and Trademarks